US012329340B2

(12) United States Patent
Trice et al.

(10) Patent No.: US 12,329,340 B2
(45) Date of Patent: Jun. 17, 2025

(54) HIGH SPEED REUSABLE BEVERAGE CONTAINER WASHING SYSTEM WITH SPINNING BEVERAGE CONTAINER HOLDER

(71) Applicant: Midea Group Co., Ltd., Foshan (CN)

(72) Inventors: Daniel J. Trice, Louisville, KY (US); Robert M. Digman, Goshen, KY (US)

(73) Assignee: MIDEA GROUP CO., LTD., Guangdong (CN)

( * ) Notice: Subject to any disclaimer, the term of this patent is extended or adjusted under 35 U.S.C. 154(b) by 291 days.

(21) Appl. No.: 17/957,868

(22) Filed: Sep. 30, 2022

(65) Prior Publication Data

US 2024/0108191 A1   Apr. 4, 2024

(51) Int. Cl.
| A47L 15/00 | (2006.01) |
| A47L 15/42 | (2006.01) |
| A47L 15/50 | (2006.01) |
| A61L 2/10 | (2006.01) |
| B65G 47/52 | (2006.01) |

(52) U.S. Cl.
CPC ....... *A47L 15/0071* (2013.01); *A47L 15/0076* (2013.01); *A47L 15/4242* (2013.01); *A47L 15/50* (2013.01); *A61L 2/10* (2013.01); *B65G 47/52* (2013.01); *A61L 2202/11* (2013.01); *A61L 2202/17* (2013.01); *A61L 2202/23* (2013.01)

(58) Field of Classification Search
CPC ...... A47L 15/50; A47L 15/503; A47L 15/505; A47L 15/0065; A47L 15/0071; A47L 2202/23; B08B 9/42
See application file for complete search history.

(56) References Cited

U.S. PATENT DOCUMENTS

| 1,502,131 A | 2/1922 | Vaudreuil |
| 1,716,406 A | 6/1929 | Wolf |
| 1,876,895 A | 9/1932 | James |
| 2,263,807 A | 11/1941 | Hanson |
| 2,634,736 A | 4/1953 | Bewen |

(Continued)

FOREIGN PATENT DOCUMENTS

| CN | 2834716 Y | 11/2006 |
| CN | 201529653 U | 7/2010 |

(Continued)

OTHER PUBLICATIONS

EP3015043A1 Machine Translation (Year: 2016).*

(Continued)

*Primary Examiner* — Spencer E. Bell
(74) *Attorney, Agent, or Firm* — Gray Ice Higdon

(57) ABSTRACT

A beverage container washing system may be used for rapid washing and/or sanitizing of beverage containers, e.g., for use in a retail environment to wash and/or sanitize customer-provided beverage containers prior to filling the beverage containers with purchased beverages, among other applications. Separate entrance and exit openings may be provided in some instances to minimize employee interaction with unwashed customer beverage containers, and a beverage container may be conveyed from the entrance opening to the exit opening past one or more stations using a holder that is capable of spinning the beverage container when the beverage container is disposed in at least one of the stations.

18 Claims, 8 Drawing Sheets

(56) References Cited

U.S. PATENT DOCUMENTS

| | | |
|---|---|---|
| 2,764,017 A | 9/1956 | Ronnebeck |
| 2,943,474 A | 7/1960 | Bochan |
| 2,970,700 A | 2/1961 | Lacy et al. |
| 3,060,946 A | 10/1962 | David |
| 3,122,148 A | 2/1964 | Alabaster |
| 3,204,273 A | 9/1965 | Gallo |
| 3,312,230 A | 4/1967 | Thring |
| 3,370,597 A | 2/1968 | Fox |
| 4,326,551 A | 4/1982 | Voorhees |
| 4,456,022 A | 6/1984 | Roberts |
| 4,561,904 A | 12/1985 | Eberhardt, Jr. |
| 4,580,421 A | 4/1986 | Babuin et al. |
| 4,634,052 A | 1/1987 | Grizzle et al. |
| 4,681,260 A | 7/1987 | Cochran |
| 4,689,089 A | 8/1987 | Eberhardt, Jr. et al. |
| 5,249,590 A | 10/1993 | Jacobus |
| 5,315,729 A | 5/1994 | Yang |
| 5,343,886 A | 9/1994 | Beswick |
| 5,531,383 A | 7/1996 | Pacht et al. |
| 5,640,981 A | 6/1997 | Niemela et al. |
| 5,675,880 A | 10/1997 | Saikin |
| 5,704,380 A | 1/1998 | Zelniker et al. |
| 5,903,944 A | 5/1999 | Burrell |
| 5,904,163 A | 5/1999 | Inoue et al. |
| 6,086,222 A | 7/2000 | Juba et al. |
| 6,110,424 A | 8/2000 | Maiden et al. |
| 6,517,776 B1 | 2/2003 | Rodgers et al. |
| 6,579,495 B1 | 6/2003 | Maiden |
| 6,691,536 B2 | 2/2004 | Severns et al. |
| 6,732,950 B2 | 5/2004 | Ingham, Jr. et al. |
| 6,799,732 B2 | 10/2004 | Sirkin |
| 6,926,017 B2 | 8/2005 | Halbmaier |
| D516,757 S | 3/2006 | Hedstrom |
| 7,236,099 B2 | 6/2007 | Schult |
| 7,550,935 B2 | 6/2009 | Lys et al. |
| 7,674,001 B1 | 3/2010 | Ferrin et al. |
| 7,882,591 B2 | 2/2011 | Arnold |
| 8,136,742 B2 | 3/2012 | Cordua |
| 8,146,612 B2 | 4/2012 | Brunswick et al. |
| 8,206,144 B2 | 6/2012 | Ng et al. |
| 8,297,533 B2 | 10/2012 | Dunn et al. |
| 8,303,728 B2 | 11/2012 | Peukert et al. |
| 8,500,919 B1 | 8/2013 | Al-qaffas |
| 8,810,423 B2 | 8/2014 | Kaczmarek et al. |
| 8,905,014 B2 | 12/2014 | Shaffer |
| 9,138,768 B2 | 9/2015 | Jahan et al. |
| 9,146,032 B2 | 9/2015 | Maxwell |
| 9,378,988 B2 | 6/2016 | Osada et al. |
| 9,474,432 B2 | 10/2016 | Alexander |
| 9,566,617 B2 | 2/2017 | Jensen et al. |
| 9,596,972 B2 | 3/2017 | Sonoda |
| 9,615,722 B2 | 4/2017 | Mesa et al. |
| 9,623,447 B2 | 4/2017 | Kataoka |
| 9,707,306 B2 | 7/2017 | Farren |
| 9,955,844 B2 | 5/2018 | Fletty et al. |
| 10,047,922 B2 | 9/2018 | Chien |
| 10,415,176 B2 | 9/2019 | Abramovich et al. |
| 10,670,619 B2 | 6/2020 | Schulze et al. |
| 10,893,790 B2 | 1/2021 | Ashworth et al. |
| 10,921,059 B2 | 2/2021 | Newland, III et al. |
| 11,166,617 B2 | 11/2021 | Yoon et al. |
| 11,241,137 B1 | 2/2022 | Ferguson et al. |
| 11,253,131 B2 | 2/2022 | Kwon |
| 2003/0150475 A1 | 8/2003 | Abrams et al. |
| 2005/0230638 A1 | 10/2005 | Ancona et al. |
| 2006/0011263 A1 | 1/2006 | Till |
| 2007/0246071 A1 | 10/2007 | Streb |
| 2011/0192808 A1* | 8/2011 | Buhl .................. A47L 15/505 |
| | | 211/41.9 |
| 2011/0203616 A1 | 8/2011 | Berner et al. |
| 2012/0141322 A1 | 6/2012 | Fogg |
| 2012/0306333 A1* | 12/2012 | Eng .................. A47J 47/16 |
| | | 211/41.9 |
| 2013/0198786 A1 | 8/2013 | Cook et al. |
| 2018/0028044 A1 | 2/2018 | Anim-Mensah et al. |
| 2018/0092505 A1 | 4/2018 | Simon |
| 2018/0236398 A1 | 8/2018 | Heer et al. |
| 2018/0318886 A1 | 11/2018 | Libbrecht et al. |
| 2018/0338665 A1 | 11/2018 | Foehringer |
| 2018/0354467 A1 | 12/2018 | Glickman et al. |
| 2019/0358682 A1 | 11/2019 | Borghi et al. |
| 2020/0216332 A1 | 7/2020 | Li |
| 2020/0253450 A1 | 8/2020 | Kafzan et al. |
| 2020/0289685 A1 | 9/2020 | Li |
| 2020/0337522 A1 | 10/2020 | Brewer et al. |
| 2021/0113054 A1 | 4/2021 | Son et al. |
| 2021/0161356 A1 | 6/2021 | Luu et al. |
| 2021/0178434 A1 | 6/2021 | Van Pottelbergh et al. |
| 2021/0259509 A1* | 8/2021 | Sperry .................. A47L 15/501 |
| 2021/0308301 A1 | 10/2021 | Sperry |
| 2022/0018531 A1 | 1/2022 | Mo et al. |
| 2022/0079413 A1 | 3/2022 | Longo et al. |
| 2022/0240750 A1 | 8/2022 | Held |
| 2022/0338706 A1 | 10/2022 | Disch |
| 2022/0409007 A1* | 12/2022 | Renz .................. A47L 15/505 |
| 2023/0095081 A1 | 3/2023 | Boyer et al. |
| 2023/0097782 A1 | 3/2023 | Trice et al. |
| 2023/0100978 A1 | 3/2023 | Boyer et al. |
| 2023/0101333 A1 | 3/2023 | Boyer et al. |
| 2023/0101384 A1 | 3/2023 | Longo et al. |
| 2023/0101450 A1 | 3/2023 | Boyer et al. |
| 2023/0102987 A1 | 3/2023 | Boyer et al. |
| 2023/0112411 A1 | 4/2023 | Digman et al. |

FOREIGN PATENT DOCUMENTS

| | | |
|---|---|---|
| CN | 102324396 A | 1/2012 |
| CN | 202529825 U | 11/2012 |
| CN | 203426095 U | 2/2014 |
| CN | 204363929 U | 6/2015 |
| CN | 205110293 U | 3/2016 |
| CN | 105534437 A | 5/2016 |
| CN | 205736064 U | 11/2016 |
| CN | 104826144 B1 | 1/2018 |
| CN | 108703731 A | 10/2018 |
| CN | 109513022 A | 3/2019 |
| CN | 109876169 A | 6/2019 |
| CN | 209915722 U | 1/2020 |
| CN | 209967112 U | 1/2020 |
| CN | 212166190 U | 12/2020 |
| CN | 212883643 U | 4/2021 |
| CN | 213191400 U | 5/2021 |
| CN | 213551016 U | 6/2021 |
| CN | 113500070 A | 10/2021 |
| CN | 215032125 U | 12/2021 |
| CN | 113953276 A | 1/2022 |
| CN | 113953280 A | 1/2022 |
| CN | 113953281 A | 1/2022 |
| CN | 216126276 U | 3/2022 |
| CN | 216454736 U | 5/2022 |
| DE | 4229250 A1 | 3/1994 |
| DE | 19618770 A1 | 11/1997 |
| DE | 102012109360 A1 | 5/2014 |
| DE | 102014222586 A1 | 5/2016 |
| DE | 102019106248 A1 | 10/2019 |
| DE | 102020112205 A1 | 11/2020 |
| DE | 102019214059 | 3/2021 |
| EP | 0577569 B1 | 4/1996 |
| EP | 1120121 A2 | 8/2001 |
| EP | 2559369 A2 | 2/2013 |
| EP | 2703724 A1 | 3/2014 |
| EP | 1970134 B1 | 7/2014 |
| EP | 3015043 A1 * | 5/2016 ......... A47L 15/0071 |
| EP | 3636333 A1 | 4/2020 |
| EP | 3788936 A1 | 3/2021 |
| EP | 3967207 A1 | 3/2022 |
| ES | 1265944 U | 4/2021 |
| FR | 1426408 A | 1/1966 |
| FR | 2765816 A1 | 1/1999 |
| FR | 3068232 A1 | 1/2019 |
| IL | 108864 A | 3/1999 |
| JP | 2001247108 A | 9/2001 |
| KR | 101630417 B1 | 6/2016 |
| KR | 20160065051 A | 6/2016 |

(56) References Cited

FOREIGN PATENT DOCUMENTS

| KR | 20180051462 A | 5/2018 |
|---|---|---|
| KR | 101885722 B1 | 9/2018 |
| KR | 101983721 B1 | 5/2019 |
| KR | 101987953 B1 | 6/2019 |
| KR | 102052837 B1 | 12/2019 |
| WO | WO2000078200 A2 | 12/2000 |
| WO | WO0244637 A1 | 6/2002 |
| WO | WO2005087276 A2 | 9/2005 |
| WO | WO2007038904 A1 | 4/2007 |
| WO | WO2010132022 A2 | 11/2010 |
| WO | WO2020083851 A1 | 4/2020 |
| WO | WO2020212927 | 10/2020 |
| WO | 2020223540 A1 | 11/2020 |

OTHER PUBLICATIONS

Related Applications Transmittal.
YBB, YBB Professional Cup Washing Machine Tables Glass Rinser, Pitcher Rinser for Bar Café Household (Counter Top), retrieved from: https://www.amazon.com/YBB-Professional-Pitcher-Plating-Household/dp/B01MG7GPIR; Oct. 31, 2016.
Jectse, Cup Rinser, Automatic Household Commercial Cup Washer High-Pressure Cup Washer Cleaner Rinser Bar Accessories Home, Restaurant, Bar, Tea Shop, Coffee Shop, etc., Retrieved from: https://www.amazon.com/Automatic-Commercial-high-Pressure-Accessories-Restaurant/dp/B0868M9J9R, Mar. 23, 2020.
Hobart, Cleaning of Reusable Cups, Retrieved from: https://www.hobart-export.com/market-solutions/industry/cup-cleaning; Retrieved on: Sep. 23, 2021.
Webstaurantstore, Champion CG4 Low Temperature 48" Pass-Through Glass Washer, Left to Right—208/230V, Retrieved from: https://www.webstaurantstore.com/champion-cg4-low-temperature-48-pass-through-glass-washer-left-to-right-208-230v/253CG4LRV.html, Retrieved on: Sep. 23, 2021.
Northern Brewer, Vinator Bottle Rinser, Retrieved from: https://www.northernbrewer.com/products/vinator-bottle-rinser, Retrieved on Sep. 27, 2021.
Babymoov, Babymoov Turbo Pure Sterilizer & Dryer (2020), KiddiesKingdom.com, Retrieved from:https://www.kiddies-kingdom.com/health-hygiene/36070-babymoov-turbo-pure-sterilizer-dryer-2020.html, 2020.
Exair, High Efficiency Fixed Aluminum Air Amplifier, Inlet Dia.: 2.0 in, Grainger.com, Retrieved from: https://www.grainger.com/product/4LCX5?ef_id=EAlaIQobChMIotPGscCI8gIVZGxvBB3KTQnjEAQYAyABEgJDjfD_BwE:G:s&s_kwcid=AL!2966!3!281698275816!!!g!469974894180!&gucid=N:N:PS:Paid, Retrieved on: Sep. 27, 2021.
SolvAir, Food & Beverage, Retrieved from: https://www.solvair.co.uk/applications/food-and-beverage/; Retrieved on: Sep. 27, 2021.
Costway, Full-Automatic Washing Machine 7.7 lbs Washer, Retrieved from: https://www.walmart.com/ip/Full-Automatic-Washing-Machine-7-7-lbs-Washer-Spinner-Germicidal-UV-Light-Blue/354269146, Retrieved on Sep. 27, 2021.
Katom, Perlick PKBR24 24" Underbar Glass Washer, Retrieved from: https://www.katom.com/199-PKBR24.html?gclid=EAlaIQobChMI_aLznJmE8gIV2wytBh3yjwltEAQYBSABEgLu_vD_BwE, Retrieved on Sep. 27, 2021.
Gosain, Gaurav, A More Sustainable Dishwasher, ME589: Sustainable Design, Dec. 16, 2013.
Dongguan Vistech Import & Export Co., LTD, Mini UV Lamp Ultraviolet Germicidal Disinfection Lamp Portable UV Handheld Home Travel Ozone Sterilizer Light, Retrieved from: https://dgvistech.en.made-in-china.com/product/eZixUMaChJkH/China-Mini-UV-Lamp-Ultraviolet-Germicidal-Disinfection-Lamp-Portable-UV-Handheld-Home-Travel-Ozone-Sterilizer-Light.html, Retrieved on Sep. 30, 2021.
UVClean, UV-C Sanitizing Light Disinfection Telescoping Room Robot: Glow Trolley, Retrieved from: https://uvcleanhouse.com/products/glow-trolley, Retrieved on Sep. 30, 2021.
Meiko, Efficient Cleaning of Cups and Bottles, Retrieved from: https://www.meiko.info/en/efficient-cleaning-of-cups-and-bottles, Retrieved on Jan. 27, 2021.
Graf, Irina, United States Patent and Trademark Office, Notice of Allowance issued in U.S. Appl. No. 17/490,869, 26 pages, dated Mar. 6, 2024.
Graf, Irina, United States Patent and Trademark Office, Non-Final Office Action issued in U.S. Appl. No. 17/490,869, 193 pages, dated Sep. 14, 2023.

* cited by examiner ated with
HIGH SPEED REUSABLE BEVERAGE CONTAINER WASHING SYSTEM WITH SPINNING BEVERAGE CONTAINER HOLDER

BACKGROUND

Due in part to the environmental concerns associated with disposable or single use beverage containers, many consumers are increasingly opting to use reusable cups, reusable bottles and other types of reusable beverage containers. In addition, some retail establishments, such as coffee shops, donut shops, and restaurants, have been willing to fill customer-provided cups and other beverage containers, and some have even introduced reusable cup programs where customers are able to purchase a reusable cup at a low initial cost when purchasing a beverage and then present that same cup at a later date for a refill.

While such programs have proven to be beneficial for both consumers and retail establishments, ensuring that the reusable cups are clean and sanitary prior to filling can be a challenge. Some municipalities, for example, have instituted ordinances that require a retail establishment to clean a work space after handling a customer-supplied reusable cup. Furthermore, pandemic-related concerns have led many retail establishments to discontinue the use of reusable cups due to the potential for a transmission of germs or contamination.

Retail establishments that serve beverages often use commercial-style dishwashers to wash cups and other utensils. Such dishwashers, however, are often configured to handle a large number of utensils in each load, and even the fastest dishwashers can still have runtimes of several minutes or more. Such dishwashers are also relatively large and noisy, and as a result are often placed in a kitchen or other area that is outside of the range of customers. As a result, traditional commercial-style dishwashers have a number of characteristics that make them generally unsuitable for use in connection with cleaning customer-provided reusable beverage containers.

Therefore, a significant need exists in the art for a system capable of washing reusable cups and other beverage containers in a fast and sanitary manner, and in particular, a system capable of being utilized in a retail establishment to clean customer-provided reusable beverage containers prior to filling, and to do so in a manner that is both fast and compatible with a fast-paced retail environment.

SUMMARY

The herein-described embodiments address these and other problems associated with the art by providing various improvements related to a beverage container washing system that may be used for rapid washing and/or sanitizing of beverage containers, e.g., for use in a retail environment to wash and/or sanitize customer-provided beverage containers prior to filling the beverage containers with purchased beverages, among other applications. Separate entrance and exit openings may be provided in some instances to minimize employee interaction with unwashed customer beverage containers, and a beverage container may be conveyed from the entrance opening to the exit opening past one or more stations using a holder that is capable of spinning the beverage container when the beverage container is disposed in at least one of the stations.

Therefore, consistent with one aspect of the invention, an apparatus for washing a beverage container may include a housing, a holder disposed within the housing and configured to hold a beverage container during a wash cycle, a plurality of stations disposed within the housing, the plurality of stations including a first station for loading the beverage container into the holder and a second station configured to perform an operation on the beverage container during the wash cycle, and a holder transfer assembly supporting the holder and configured to transfer the holder between the plurality of stations, where the holder transfer assembly is further configured to spin the holder and thereby spin the beverage container during at least a portion of the transfer of the holder between the plurality of stations.

In some embodiments, the holder transfer assembly includes a holder support configured to rotatably support the holder, a holder support drive configured to move the holder support along a path extending between the plurality of stations, a pinion gear operably coupled to the holder to rotate with the holder, and a rack gear extending along at least a portion of the path extending between the plurality of stations and positioned to engage the pinion gear such that movement of the holder support along the path while the pinion gear engages the rack gear additionally rotates the holder.

Also, in some embodiments, the path and the rack gear are substantially linear and the holder support drive includes a linear actuator. Further, in some embodiments, the linear actuator includes a screw drive. In some embodiments, the holder transfer assembly further includes a conveyor configured to support the holder support, and the holder support drive is configured to move the holder support along the path extending between the plurality of stations by moving the conveyor. In addition, in some embodiments, the rack gear includes at least one toothless section such that no rotation of the holder occurs during movement of the holder support along the path proximate the toothless section of the rack gear. In some embodiments, the first station is a loading and unloading station.

In addition, in some embodiments, the housing includes an entrance opening and an exit opening that is separate from the entrance opening, the entrance opening configured to receive a beverage container prior to the wash cycle and the exit opening configured to provide access to the beverage container after the wash cycle, the first station is a loading station disposed proximate the entrance opening and the plurality of stations further includes an unloading station disposed proximate the exit opening. Moreover, in some embodiments, the second station includes a washing station, an ultraviolet sanitizing station or a drying station. In some embodiments, the second station includes a washing station and the plurality of stations further includes an ultraviolet sanitizing station or a drying station. Moreover, in some embodiments, the second station includes a washing station and the plurality of stations further includes an ultraviolet sanitizing and drying station. In some embodiments, the second station includes an ultraviolet sanitizing station, and the holder transfer assembly is configured to spin the holder and thereby spin the beverage container during at least a portion of the transfer of the holder through the ultraviolet sanitizing station.

In addition, in some embodiments, the holder is configured to support the beverage container in an inverted orientation. In some embodiments, the holder is configured to receive the beverage container via manual insertion, and the holder is configured to allow for manual removal of the beverage container. Moreover, in some embodiments, the holder includes a base configured to support the beverage container when the beverage container is held by the holder in an inverted orientation, and a retainer configured to support a sidewall of the beverage container when the beverage container is held by the holder in the inverted orientation to restrict lateral movement of the beverage container during the washing cycle, the retainer including a lateral opening through which the beverage container may be passed during insertion into and/or removal from the holder.

Also, in some embodiments, the retainer includes a C-shaped retaining ring vertically separated from the base, and the lateral opening is at least partially defined by an opening in the C-shaped retaining ring. In some embodiments, the retainer further includes first and second generally vertical supports supporting the C-shaped retaining ring and positioned on an opposite side of the base from the opening in the C-shaped retaining ring, and the lateral opening is at least partially defined by the first and second generally vertical supports at an elevation below that of the C-shaped retaining ring such that a width of a first portion of the lateral opening below the C-shaped retaining ring is greater than a width of a second portion of the lateral opening defined by the opening in the C-shaped retaining ring. In addition, in some embodiments, the base includes an inclined portion defining a plurality of concentric annular supports, each of the plurality of concentric annular supports configured to center the beverage container in the holder when the beverage container is held by the holder in the inverted orientation. Also, in some embodiments, the base includes a plurality of steps defining a plurality of concentric annular supports, each of the plurality of concentric annular supports configured to center the beverage container in the holder when the beverage container is held by the holder in the inverted orientation.

Consistent with another aspect of the invention, an apparatus for washing a beverage container may include a housing including an entrance opening and an exit opening that is separate from the entrance opening, the entrance opening configured to receive a beverage container prior to a wash cycle and the exit opening configured to provide access to the beverage container after the wash cycle, a holder disposed within the housing and configured to hold the beverage container during the wash cycle, a plurality of stations disposed within the housing, the plurality of stations including a loading station disposed proximate the entrance opening for loading the beverage container into the holder, an unloading station disposed proximate the exit opening for unloading the beverage container from the holder, at least one intermediate station between the loading and unloading stations and configured to perform an operation on the beverage container during the wash cycle, and a holder transfer assembly supporting the holder and configured to transfer the holder between the loading, at least one intermediate, and unloading stations. The holder transfer assembly may further include a holder support configured to rotatably support the holder, a holder support drive configured to move the holder support along a path extending between the plurality of stations, a pinion gear operably coupled to the holder to rotate with the holder, and a rack gear extending along at least a portion of the path extending between the plurality of stations and positioned to engage the pinion gear such that movement of the holder support along the path while the pinion gear engages the rack gear additionally rotates the holder.

Other embodiments may include various methods for making and/or using any of the aforementioned constructions.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

DETAILED DESCRIPTION

Figure 1:
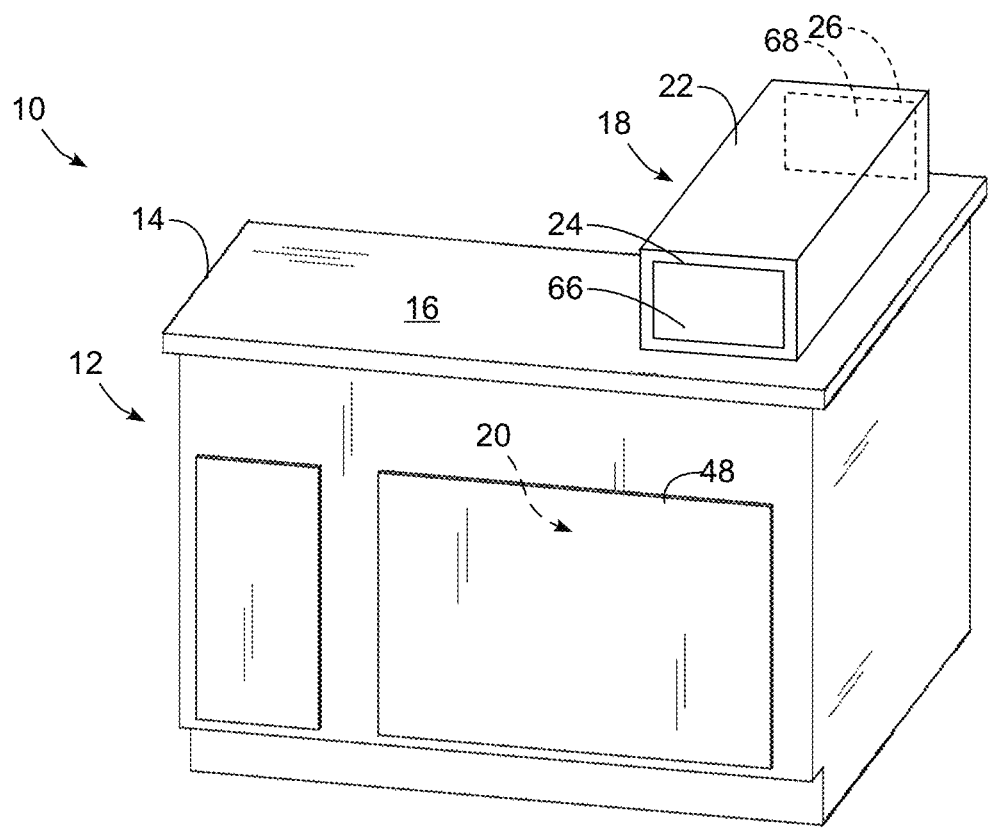
FIG. 1 is a perspective view of an example beverage container washing system consistent with the invention.

In some embodiments consistent with the invention, a beverage container washing system may be used to rapidly wash beverage containers, including, for example, reusable beverage containers such as may be provided by customers of a retail establishment.

A beverage container, in this regard, may be considered to be any type of container that is capable of holding a beverage for consumption, including, for example, a cup, a bottle, a bowl, etc. A beverage container may generally include a mouth or opening defined by a lip, and may or may not include a cap, a lid or other form of closure. A beverage container may be reusable to the extent that the beverage container may be reused multiple times, in contrast with a disposable or single use beverage container that is generally thrown away after use.

A beverage container washing system consistent with some embodiments of the invention may be used to wash or clean a beverage container. In some embodiments, a beverage container washing system may also be considered to be a sanitizing system that is also capable of sanitizing a beverage container to inactivate, reduce or destroy microorganisms on the surface of the beverage container, e.g., bacteria and other pathogenic organisms. Sanitization may be achieved through the use of high temperatures, ultraviolet irradiation, disinfecting agents, or some combination of the same, such that a sanitizing operation may be considered to be a particular type of washing operation where some degree of sanitization occurs in addition to washing or cleaning. It will be appreciated, however, that some of the concepts disclosed herein may be utilized in connection with washing systems that, while capable of washing or cleaning a beverage container, are not considered to sanitize the beverage container to the extent required to consider the beverage container as being sanitized at the completion of a washing operation.

It will also be appreciated that a beverage container washing system consistent with the invention may be, but is not necessarily, used in a retail environment (e.g., a bar, a coffee shop, a restaurant, etc.) to rapidly wash the beverage container of a customer prior to filling the beverage container with a beverage that has been purchased by a customer, e.g., in some instances, less than one minute, and in some instances, about 30 seconds or less. Further, a beverage container washing system consistent with the invention may be, but is not necessarily, used to rapidly wash a single, individual beverage container in a washing operation. In other embodiments, for example, some of the concepts disclosed herein may be utilized in non-retail environments, including within a consumer's home, an office environment, or any other environment for which it may be desired to wash beverage containers. Further, even within a retail environment, a washing system consistent with the invention may be used in non-customer facing applications, e.g., behind the counter, in the kitchen, etc. Further, some of the concepts disclosed herein may be adapted for use in connection with washing multiple beverage containers in a single washing operation, as well as washing operations that take one or more minutes to complete.

In the example embodiment discussed hereinafter, hot water (e.g., about 150 degrees/65 degrees Celsius or higher in some embodiments, or about 165 degrees Fahrenheit/74 degrees Celsius or higher in some embodiments), high pressure (e.g., about 100 psi or greater), high speed air for drying, and ultraviolet irradiation are used to rapidly wash and sanitize an individual beverage container, e.g., in about 30 seconds, and do so in a manner that has a minimal countertop space presence. Furthermore, in order to minimize interaction between a customer and retail establishment employee, separate entrance and exit openings are used, such that the opening in which a customer inserts an unwashed beverage container into the system prior to performing a washing operation is different from the opening in which a retail establishment employee removes the washed beverage container at the completion of the washing operation. A washing system consistent with the invention may move the beverage container between multiple stations to perform different actions, and in some instances, operate on different beverage containers concurrently in different stations. It will be appreciated, however, that in other embodiments, a washing system consistent with the invention may use the same opening for insertion and removal of a beverage container, and may operate on multiple beverage containers at the same time. Further, in some embodiments, lower temperatures and/or pressures may be used, and ultraviolet irradiation and/or drying may be omitted, or additional actions, such as the introduction of detergents, disinfecting agents, etc. may be used. Therefore, the invention is not limited to the specific embodiments disclosed herein.

Now turning to the drawings, wherein like parts are denoted by like numbers throughout the several views, FIG. 1 illustrates a beverage container washing system or apparatus 10 consistent with some embodiments of the invention, and suitable for installation, for example, in a cabinet 12 that forms a counter 14 in a retail establishment. In the illustrated embodiment, washing system 10 may also be considered to be a sanitizing system 10 due to the use of hot water and/or ultraviolet irradiation, so these terms may be used interchangeably. It will be appreciated, however, that the reference to a particular concept used in a sanitizing system or in connection with a sanitizing operation does not necessarily mean that the concept cannot also be used in washing system or in connection with washing operations that are not necessarily considered sufficient for full sanitization of a beverage container.

Counter 14 includes a countertop 16, and washing system 10 includes a countertop portion 18 that projects above countertop 16 and an undercounter portion 20 that is predominantly mounted within cabinet 12 to minimize the amount of countertop space occupied by countertop portion 18. In other embodiments, washing system 10 may be fully implemented in a countertop, standalone or undercounter configuration, so the invention is not limited to the particular combination of countertop and undercounter portions as illustrated herein. In some embodiments, the countertop portion may be fixed to a countertop, but he undercounter portion may be separated, or may be mounted on a cart to simplify installation and service.

Countertop portion 18 generally includes a housing 22 having a pair of openings 24, 26, with opening 24 operating as an entrance through which a beverage container is inserted or received prior to performing a washing operation and opening 26 operating as an exit through which a beverage container is accessed or removed after performing a washing operation. Through the use of separate openings 24, 26, handling of unwashed beverage containers by retail establishment employees may be reduced or eliminated. In other embodiments, however, a single entrance/exit opening may be used.

Figure 2:
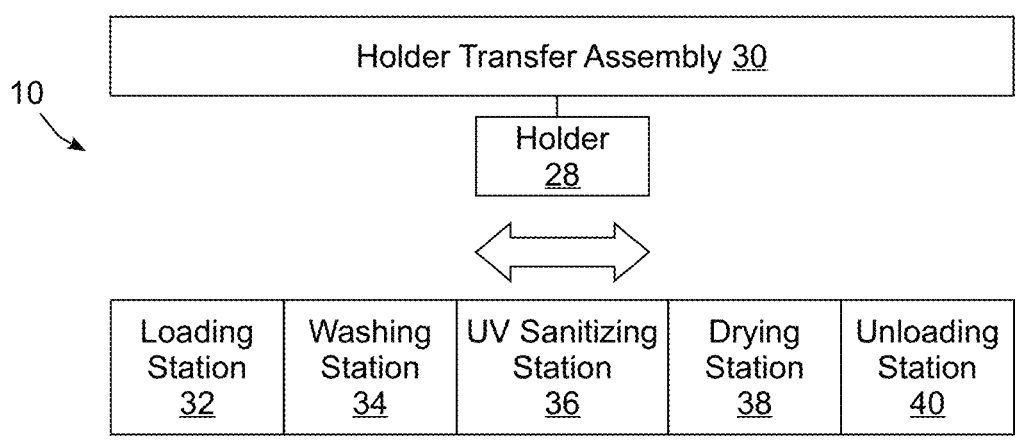
FIG. 2 is a block diagram of a plurality of stations in beverage container washing system of FIG. 1.

With additional reference to FIG. 2, which functionally illustrates various components and stations that may be implemented in beverage container washing system 10, beverage container washing system 10 is configured as a multi-station beverage container washing system, whereby countertop portion 18 also includes a holder 28 that is disposed within housing 22 and is configured to hold a beverage container as it is transferred between multiple stations during a washing or sanitizing operation. A holder transfer assembly 30 is used to move the holder 28 between a plurality of stations, including, for example, a loading station 32, a washing station 34, an ultraviolet (UV) sanitizing station 36, a drying station 38 and an unloading station 40. As will become more apparent below, holder transfer assembly is further configured to spin the holder, and thereby spin the beverage container during at least a portion of the transfer of the holder between the stations. It will be appreciated that in other embodiments, different stations may be included, some stations may be omitted (e.g., where UV sanitizing and/or drying are omitted), and/or some stations may be combined (e.g., where UV sanitizing occurs in the same station as drying and/or washing, or where loading or unloading are performed from the same station where one or more wash cycle operations are performed). Further, in some embodiments, multiple stations may perform different aspects of a particular action (e.g., separate wash and rinse stations).

In addition, and with additional reference to FIG. 3, a number of assemblies 42, 44, 46 are also utilized for performing various actions on the beverage container during a washing or sanitizing operation, and are controlled by a controller 48, which will be discussed in greater detail below.

First, a spray assembly 42 including one or more sprayers is disposed within housing 22, e.g., within washing station 34, and configured to spray a wash fluid onto the beverage container while the beverage container is held by holder 28. The wash fluid may be water in some instances, while in other instances, the wash fluid may include various agents such as detergents, disinfecting agents, etc. As will become more apparent below, when sanitization is desired, the wash fluid sprayed by the spray assembly 42 may be heated to a sanitizing temperature, e.g., about 150 degrees Fahrenheit or higher in some embodiments, and about 165 degrees Fahrenheit or higher in some embodiments, and in some instances may be pressurized at a high pressure, e.g., about 100 psi or above. Second, an ultraviolet sanitizing assembly 44 including one or more ultraviolet lights is disposed within housing 22, e.g., within UV sanitizing station 36, and configured to emit ultraviolet light toward the beverage container while the beverage container is held by holder 28. Third, a dryer assembly 46 including one or more air outlets or air knives is disposed within housing 22, e.g., within drying station 38, and configured to blow air onto the beverage container while the beverage container is held by holder 28. A number of other components in each of these assemblies, as noted above, may be disposed within cabinet 12, and may be accessed, for example, through one or more cabinet doors 48 (FIG. 1).

Figure 3:
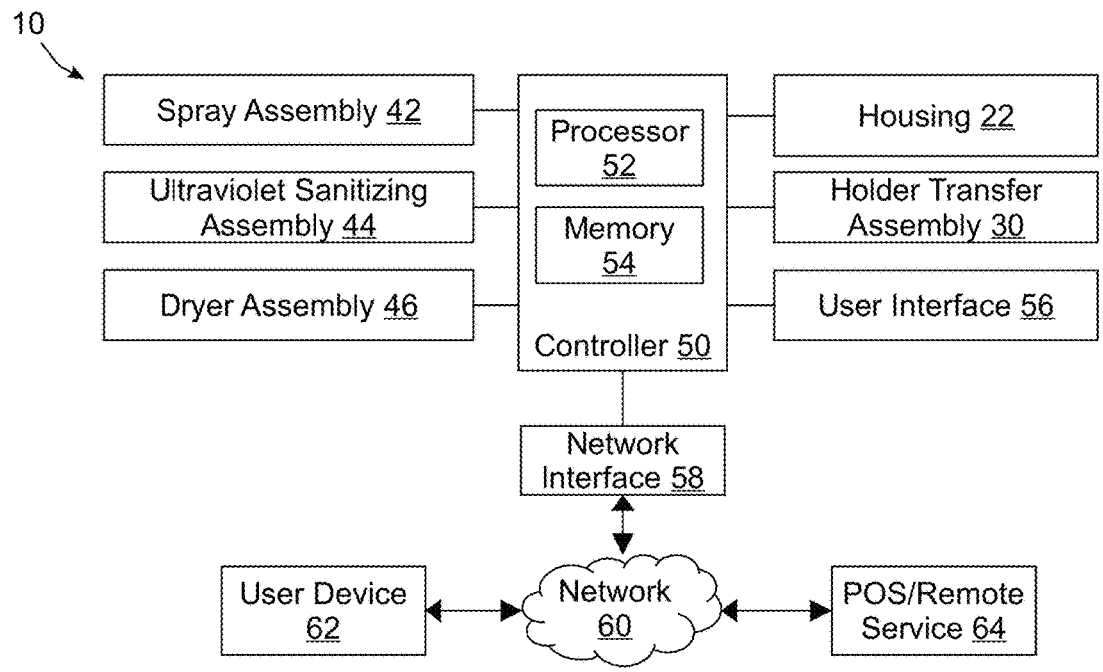
FIG. 3 is a block diagram of an example control system for the beverage container washing system of FIG. 1.

Now turning specifically to FIG. 3, washing system 10 may be under the control of a controller 50 that receives inputs from a number of components and drives a number of components in response thereto. Controller 50 may, for example, include one or more processors 52 and a memory 54 within which may be stored program code for execution by the one or more processors 52. The memory may be embedded in controller 50, but may also be considered to include volatile and/or non-volatile memories, cache memories, flash memories, programmable read-only memories, read-only memories, etc., as well as memory storage physically located elsewhere from controller 50, e.g., in a mass storage device or on a remote computer interfaced with controller 50. Controller 50 may also be implemented as a microcontroller in some embodiments, and as such these terms are used interchangeably herein. Controller 50 may also include discrete circuit logic in some embodiments, e.g., including passive and/or active circuit components.

As shown in FIG. 3, controller 50 may be interfaced with various components, including spray assembly 42, ultraviolet sanitizing assembly 44, and dryer assembly 46, as well as housing 22 and/or holder transfer assembly 30. In addition, one or more user interfaces 56, e.g., including various input/output devices such as knobs, dials, sliders, switches, buttons, lights, textual and/or graphics displays, touch screen displays, speakers, image capture devices, microphones, etc., may be used for receiving input from and communicating with one or more users. Separate user controls and/or displays may be provided, for example, on or near housing 22 for a customer and a retail establishment employee (e.g., to start or stop a washing operation), and in some instances, additional controls and/or displays may be provided at different locations, e.g., under countertop 16 or behind a cabinet door 48, to perform additional operations, such as initializing and/or shutting off the system, flushing the system, displaying error conditions, etc.

In some embodiments, controller 50 may also be coupled to one or more network interfaces 58, e.g., for interfacing with external devices via wired and/or wireless networks 60 such as Ethernet, Bluetooth, NFC, cellular and other suitable networks. It may be desirable, for example, to interface with one or more user devices 62, e.g., a customer's mobile phone, to enable a customer to start a washing operation, in some instances in connection with ordering and/or paying for a beverage. It may also be desirable to interface with various backend devices such as a point of sale (POS) system and/or a remote service 64. Moreover, in some embodiments, at least a portion of controller 50 may be implemented externally, e.g., within a mobile device, a cloud computing environment, etc., such that at least a portion of the functionality described herein is implemented within the portion of the controller that is externally implemented.

In some embodiments, controller 50 may operate under the control of an operating system and may execute or otherwise rely upon various computer software applications, components, programs, objects, modules, data structures, etc. In addition, controller 50 may also incorporate hardware logic to implement some or all of the functionality disclosed herein. Further, in some embodiments, the sequences of operations performed by controller 50 to implement the embodiments disclosed herein may be implemented using program code including one or more instructions that are resident at various times in various memory and storage devices, and that, when read and executed by one or more hardware-based processors, perform the operations embodying desired functionality. Moreover, in some embodiments, such program code may be distributed as a program product in a variety of forms, and that the invention applies equally regardless of the particular type of computer readable media used to actually carry out the distribution, including, for example, non-transitory computer readable storage media. In addition, it will be appreciated that the various operations described herein may be combined, split, reordered, reversed, varied, omitted, parallelized and/or supplemented with other techniques known in the art, and therefore, the invention is not limited to the particular sequences of operations described herein.

As noted above, controller 50 may be interfaced in some embodiments with one or both of housing 22 and holder transfer assembly 30. In the embodiment illustrated in FIGS. 1-2, for example, washing system 10 includes one or more doors 66, 68 that may be selectively actuated to open or close, e.g., to close at the beginning of a wash cycle and to open at the end of a wash cycle. Moreover, holder transfer assembly 30 is used to transfer holder 28 between the various stations illustrated in FIG. 2, as well as to return to loading station 32 after a wash cycle is complete and the clean beverage container has been removed from holder 28. It may also be desirable to include lights, indicators, displays and/or user controls on housing 22. In other embodiments, however, no mechanical manipulation of a housing may be used, whereby controller 50 may not be electronically coupled to housing 22. For example, it may be desirable in some embodiments to keep an entrance opening and an exit opening open at all times, or to use a manually or mechanically actuated closure.

Spray, ultraviolet sanitizing and dryer assemblies 42, 44, 46 may operate in various manners in different embodiments. For example, various components suitable for implementing such assemblies, as well as various undercounter components and other features that may be implemented in a beverage container washing system consistent with the invention are described in U.S. patent application Ser. No.

17/490,879, which was filed on Sep. 30, 2021 by Digman et al. and is assigned to the same assignee as the present application, and which is incorporated by reference herein.

Figure 4:
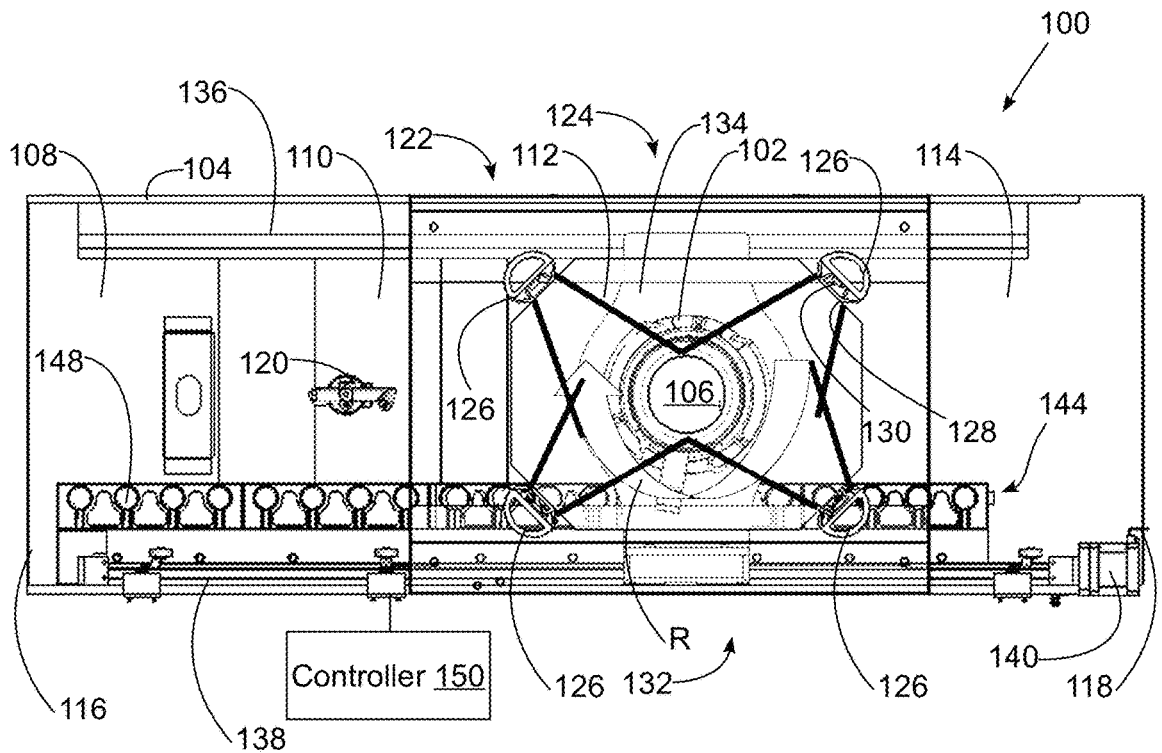
FIG. 4 is a top plan view of another example beverage container washing system consistent with the invention, and with an exterior cover removed therefrom.
Figure 5:
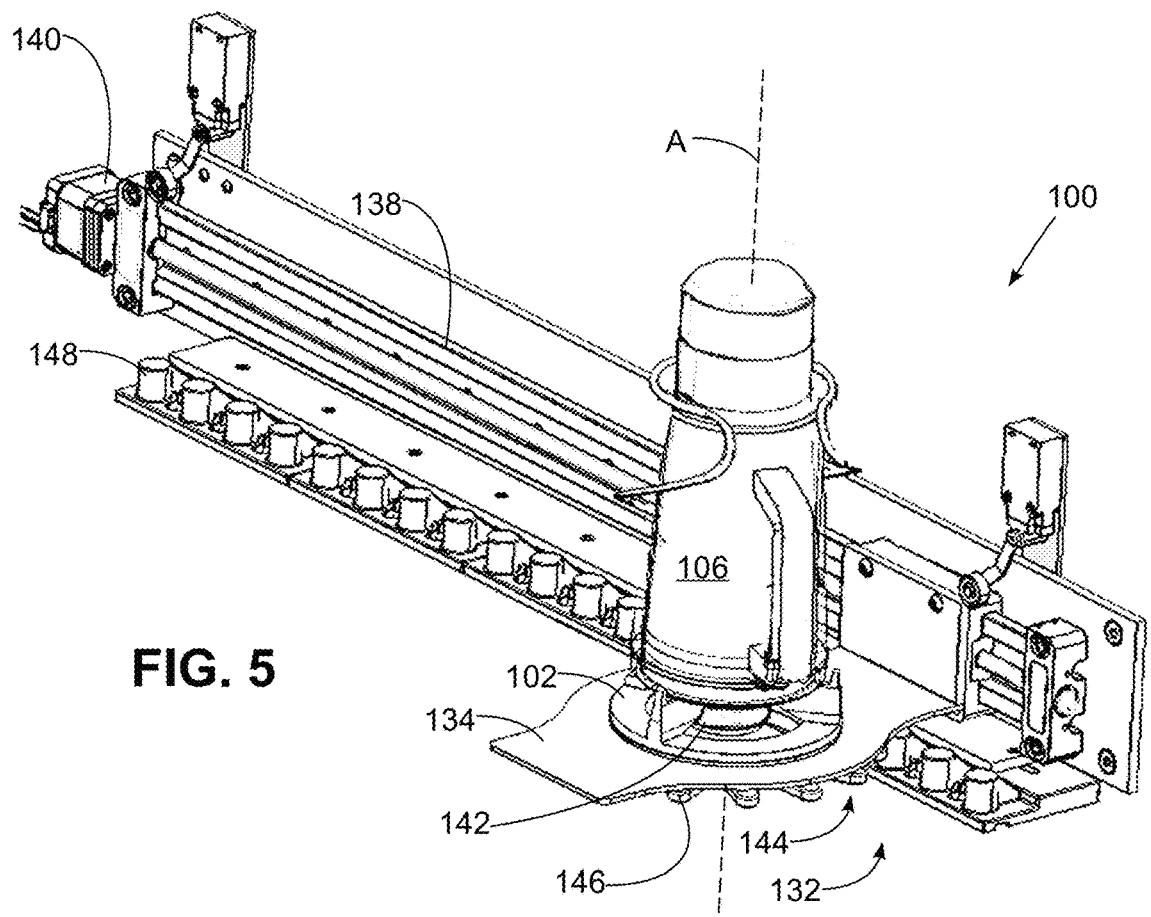
FIG. 5 is a perspective view of the holder transfer assembly of the beverage container washing system of FIG. 4.
Figure 6:
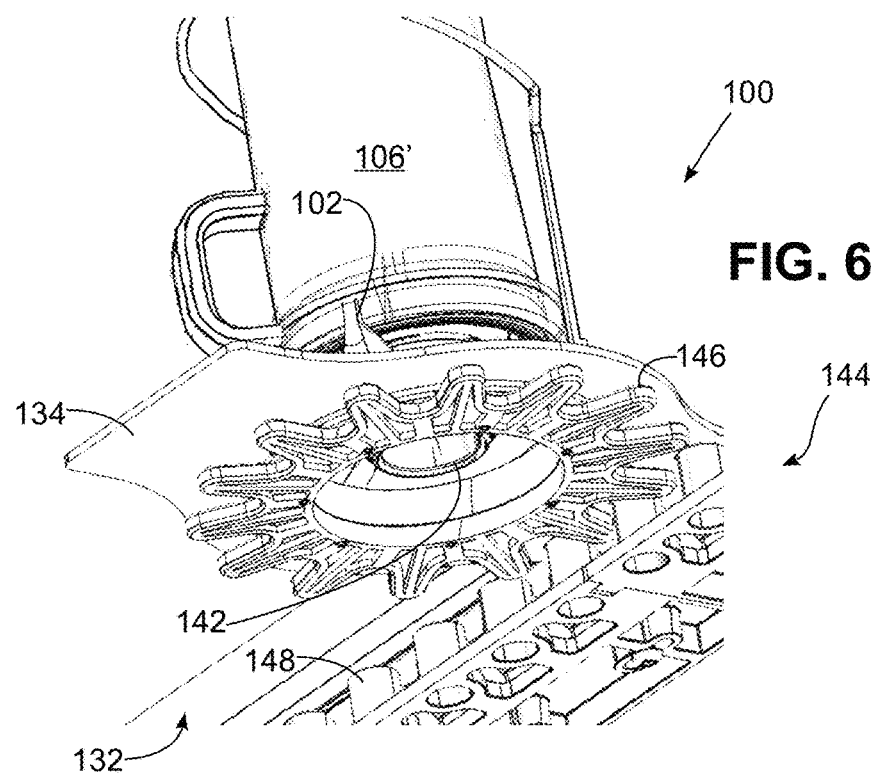
FIG. 6 is another perspective view of a portion of the holder transfer assembly of FIG. 5.

Now turning to FIGS. 4-6, as discussed above, in some embodiments it may be desirable to utilize a holder transfer assembly to spin a holder, and thus a beverage container held thereby, during at least a portion of the transfer of the holder between the various stations of a multi-station beverage container washing system. Spinning, in this regard, generally refers to rotation of a beverage container while the beverage container is being transferred to and/or from a station, and/or while the beverage container is being operated upon within a station as part of a wash cycle. In many instances, such spinning is performed to present different orientations of the beverage container to an operational assembly of the beverage container washing system while the beverage container is passing thorough and/or positioned within an operational station of the beverage container. In this regard, an operational station generally refers to a station where an operation is performed on a beverage container as part of a wash cycle, whereas an operational assembly refers to an assembly used to perform on or more operations associated with a wash cycle, e.g., washing, rinsing, drying, sanitizing, etc.

In addition, while the invention is not so limited, spinning in some embodiments may refer to rotation of a beverage container about a substantially vertical axis of the beverage container, e.g., when the beverage container is placed on a horizontal surface with its opening facing upwards, or when the beverage container is placed in an inverted orientation in a holder.

FIGS. 4-6, in particular, illustrate another example beverage container washing system 100 in greater detail. As illustrated in FIG. 4, beverage container washing system 100, similar to beverage container washing system 10, is a multi-station beverage container washing system, and includes a holder 102 disposed within a housing 104 (the cover of which has been removed) and configured to hold a beverage container 106 during a wash cycle (FIG. 6 also illustrates an alternate beverage container 106' that may also be held by holder 102). In this embodiment, four stations are utilized: a loading station 108, a washing station 110, a combined drying/ultraviolet sanitizing station 112 and an unloading station 114. Washing station 110 and drying/ultraviolet sanitizing station 112 are examples of operational stations that perform various operations associated with a wash cycle, and are also considered to be intermediate stations insofar as they are intermediate loading station 108 and unloading station 114.

Loading station 108 is disposed proximate an entrance opening 116 at one end of housing 104 for receiving beverage container 106 prior to a wash cycle, while unloading station 114 is disposed proximate an exit opening 118 at the opposite end of housing 104 for providing access to beverage container 106 after the wash cycle. It will be appreciated that in some embodiments, opening 118 and unloading station 114 may be omitted, whereby loading station 108 would serve as both a loading and unloading station.

Washing station 110 includes a sprayer 120 that is used to spray internal and/or external surfaces of beverage container, while drying/ultraviolet sanitizing station includes a drying assembly 122 and an ultraviolet sanitizing assembly 124, which in the illustrated embodiment, are each integrated into four towers 126, each of which including an air knife 128 and an ultraviolet light 130.

With additional reference to FIGS. 5-6, holder 102 is operably coupled to a holder transfer assembly 132 including a carriage 134 that functions as a holder support and that is supported on opposing rails 136, 138. A holder support drive 140, e.g., a linear actuator such as a screw drive, is operably coupled to carriage 134 to controllably move carriage 134 in a substantially linear path between stations 108-114.

In addition, carriage 134 rotatably supports holder 102, e.g., through a bearing 142 such that holder 102, and thus beverage container 106, is rotatable about an axis A (FIG. 5). In order to spin the holder, a rack and pinion gear arrangement 144, including a pinion gear 146 and a rack gear 148, is provided. Pinion gear 146, in particular, is operably coupled to holder 102 to rotate with the holder, while rack gear 148 is mounted within housing 104 to extend along at least a portion of the path extending between stations 108-114. Pinion gear 146 engages with rack gear 148 such that movement of carriage 134 along the path while the gears are engaged rotates holder 102, and thus beverage container 106, about axis A, and as represented by arrow R of FIG. 4.

In operation, a controller 150 initially moves carriage 134 to loading station 108 and awaits manual insertion of beverage container 106 into holder 102. Upon initiating a wash cycle, e.g., in response to user input through a user interface, controller 150 may actuate holder support drive 140 to transition carriage 134 to washing station 110 and then activate sprayer 120 to wash the beverage container. During the transition, and as carriage 134 moves through the washing station, holder 102 is rotated by the engagement of gears 146, 148. In some instances, holder support drive 140 may stop carriage 134 for a period of time, e.g., to position the beverage container over sprayer 120 to increase the duration of a wash portion of the wash cycle.

Next, controller 150 may actuate holder support drive 140 to transition carriage 134 to drying/ultraviolet sanitizing station 112. Sprayer 120 may also be activated and drying assembly 122 and ultraviolet sanitizing assembly 124 may be activated, at various points between this transition. As carriage 134 passes through station 112, holder 102 and beverage container 106 spin or rotate to expose different surfaces to the drying assembly 122 and ultraviolet sanitizing assembly 124. As with the washing station, in some instances holder support drive 140 may also stop carriage 134 for a period of time, e.g., to position the beverage container in the center of towers 126 to increase the duration of drying and sanitizing portions of the wash cycle.

Next, controller 150 may actuate holder support drive 140 to transition carriage 134 to unloading station 114, and drying assembly 122 and ultraviolet sanitizing assembly 124 may be deactivated at various points during this transition. The wash cycle is then complete, and the controller may await manual removal of beverage container 106 from holder 102. Once the beverage container is removed, and, for example, after user input is received to reset the washing system for a next wash cycle, controller 150 activates holder support drive 140 to return carriage 134 to the loading station 108.

It will be appreciated that various modifications may be made to the holder transfer assembly in various embodiments. For example, rather than a substantially linear path, a curvilinear path and track gear may be defined. In addition, other types of holder support drives may be used, including other types of linear actuators, or various types of pneumatic, hydraulic, electromechanical, magnetic, etc. drives may be used.

Figure 7:
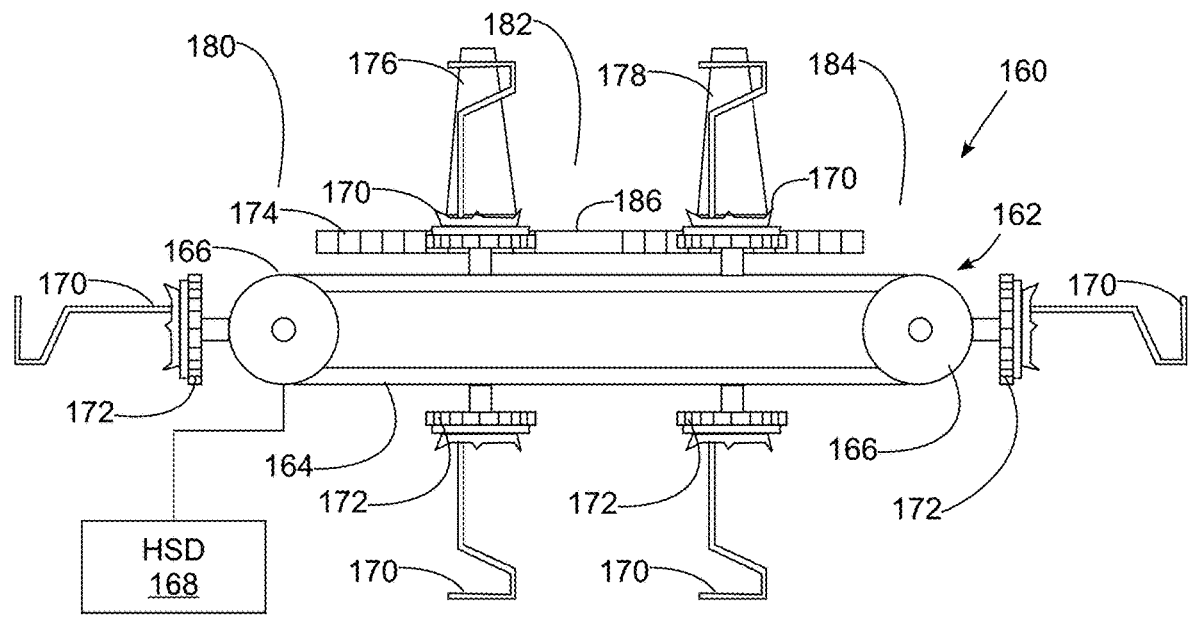
FIG. 7 is a functional side elevation view of another example beverage container washing system consistent with the invention.

In addition, as illustrated in FIG. 7, various alternate types of holder transfer assemblies may be used in other embodiments. Specifically, a beverage container washing system 160 in some embodiments may utilize a holder transfer assembly 162 configured as a conveyor, including a belt 164 and one or more drive wheels 166 driven by a holder support drive 168 (e.g., an electrical motor). Also in this embodiment, multiple holders 170 are rotatably supported by holder transfer assembly 162, and each includes a respective pinion gear 172 that engages, during a portion of the path traversed by the holders 170, a rack gear 174 to selectively spin the holder 170, and thus the beverage container (e.g., beverage containers 176, 178) held thereby.

In this embodiment, multiple beverage containers may be advanced through multiple stations (e.g., loading, washing, and unloading stations 180, 182, 184) sequentially. Moreover, the conveyor may only operate in a single direction, such that holders are returned to the loading station on the underside of the conveyor.

It will be appreciated that while the overall path for a holder 170 forms a loop, rack gear 174 extends along only a portion of the path, such that a holder 170 is only spun when its respective pinion gear 172 engages rack gear 174. Moreover, it will be appreciated that if it is desirable to not spin a beverage container even when a holder 170 and its respective pinion gear 172 are adjacent rack gear 174, rack gear 174 may be provided within one or more toothless sections, e.g., toothless section 186, where no teeth are present, and thus pinion gear 172 is not caused to rotate as the holder traverses along the path opposite the toothless section.

Other holder transfer assembly designs will be appreciated by those of ordinary skill having the benefit of the instant disclosure, e.g., where rotation of a holder is implemented independently of movement of the holder along a path. In addition, it will be appreciated that providing toothless sections of a rack gear and/or extending a rack gear only along a portion of the path traversed by a holder may be used in other embodiments, e.g., in beverage container washing system 100 discussed above.

Figure 8:
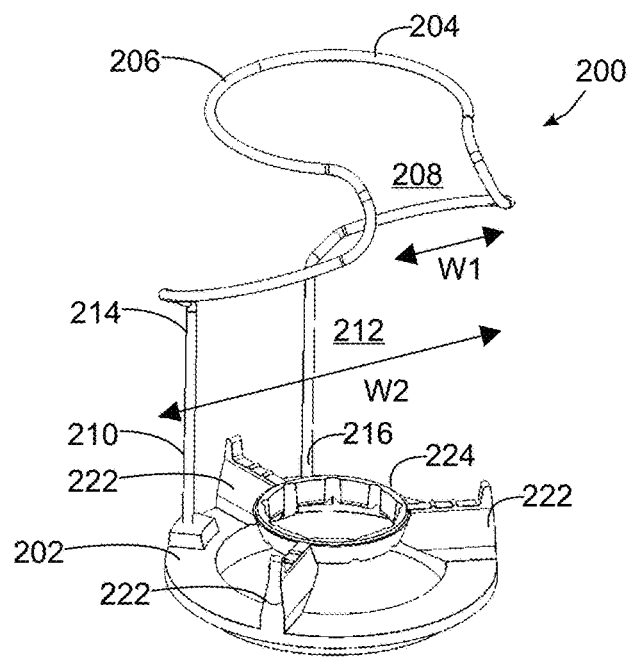
FIG. 8 is a perspective view of the holder of FIGS. 4-6.

It will be appreciated that various types of holders may be used in different embodiments to support different types of beverage containers. One such holder, including opposing grippers that are spring biased and include lateral separations to facilitate insertion and/or removal of a beverage container, as disclosed in the aforementioned cross-referenced application, may be used. FIG. 8, for example, illustrates a holder 200 that includes a base 202 configured to support a beverage container when the beverage container is held by the holder in the inverted orientation, and a retainer 204 configured to support a sidewall of the beverage container when the beverage container is held by the holder in the inverted orientation to restrict lateral movement of the beverage container during the washing operation. The retainer 204 includes a C-shaped retaining ring 206 that is vertically separated from base 202 and includes a first opening 208 having a first width W1, as well as a retaining ring support 210 supporting C-shaped retaining ring 206 on base 202 on a side opposite opening 208 and defining a second opening 212 that is intermediate first opening 208 and base 202 and that has a second width W2 that is greater than first width W1. C-shaped retaining ring 206 and retaining ring support 210 in some embodiments may be integrally formed into a single bent or formed wire that includes a pair of vertical portions 214, 216 that define vertical supports that support the C-shaped retaining ring 206 on base 202.

Figure 9:
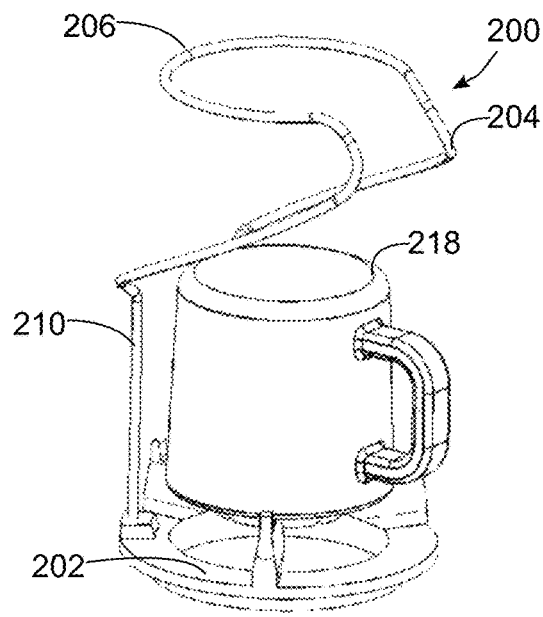
FIG. 9 illustrates a mug held by the holder of FIG. 8.
Figure 10:
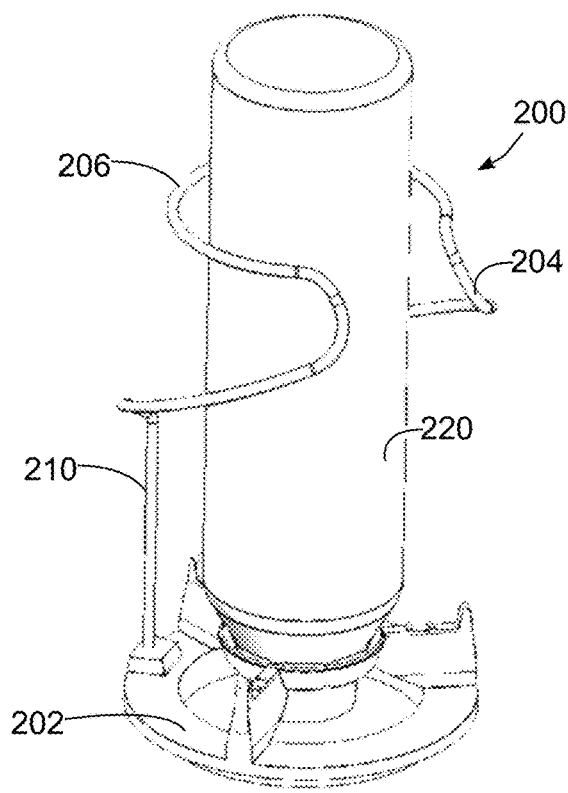
FIG. 10 illustrates a bottle held by the holder of FIG. 8.

By providing a C-shaped retaining ring, additional lateral support may be provided for taller beverage containers, and moreover, given that shorter beverage containers may have less of a need for lateral support, providing a retaining ring support that has a larger effective opening width than the C-shaped retaining ring allows for wider, shorter beverage containers to be accommodated. FIG. 9, for example, illustrates a short, wide beverage container, here a mug 218, that is supported by holder 200, but that does not extend all of the way to the elevation of C-shaped retaining ring 206, while FIG. 10 illustrates a taller, narrow beverage container, here a bottle 220, that extends through C-shaped retaining ring 206 and is thus laterally supported by the C-shaped retaining ring.

Returning to FIG. 8, base 202 in the illustrated embodiment may be formed of plastic, although other materials, e.g., various metal or wire configurations, may be used in other embodiments. Base 202 includes a plurality of (e.g., three) lip supports 222 that together operate as a substantially horizontal portion of the base to support the lip of a wide mouth beverage container, e.g., mug 218 as illustrated in FIG. 18. Lip supports 222 additionally support a central stabilizer ring 224 that operates as a substantially vertical portion of the base to support the shoulder of a narrow mount beverage container, e.g., bottle 220 as illustrated in FIG. 10.

Figure 11:
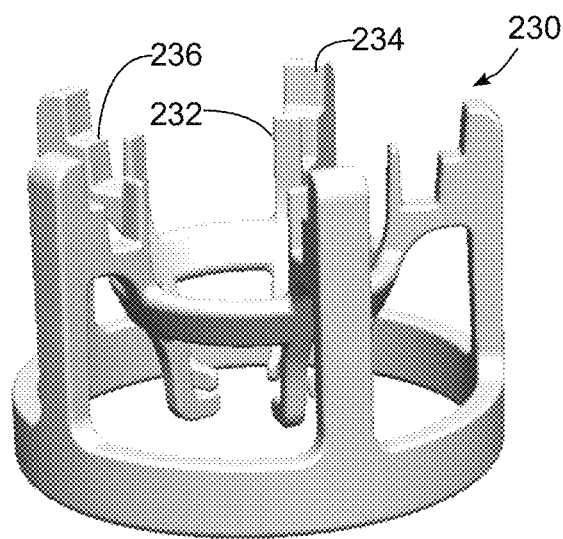
FIGS. 11-14 are perspective views of additional alternate holders to that of FIG. 8.

Additional potential holder designs are illustrated in FIGS. 11-14. FIG. 11, for example, illustrates a holder 230 including a base 232 having an inverted wedding cake design to capture various beverage containers of different mouth sizes. Base 232, in particular, has an inclined portion 234 that defines a plurality of concentric annular supports capable of centering a beverage container in the holder. Moreover, in some embodiments, the inclined portion 234 may include a plurality of discrete steps 236. Base 232 may be molded plastic in some embodiments, and may be formed of a wire frame in other embodiments.

Figure 12:
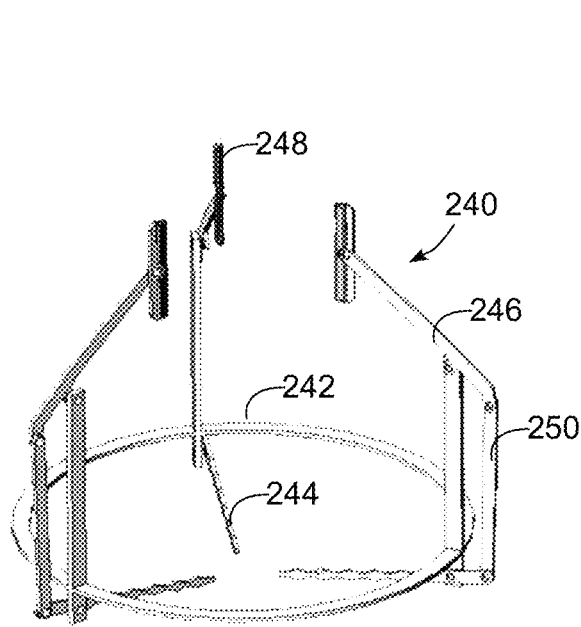

FIG. 12 illustrates a holder 240 including a base 242 with a plurality of base members 244 and a retainer 246 with a plurality of retainer members 248 configured to support the sidewall of a beverage container when the beverage container is held by the holder in the inverted orientation. In this design, base members 244 and retainer members 248 are joined by mechanical linkages 250 (e.g., planar quadrilateral linkages) such that a weight of the beverage container when supported on the plurality of base members 244 urges the plurality of retainer members 248 toward the sidewall of the beverage container.

Figure 13:
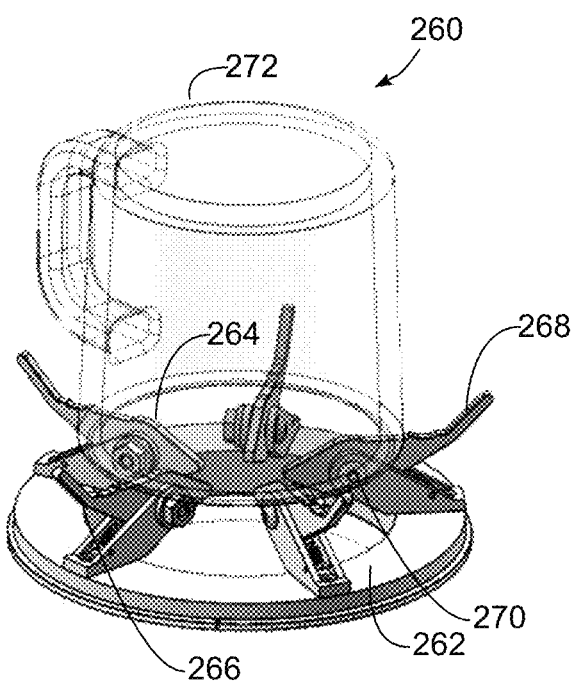

FIG. 13 illustrates a similar holder 260 including a base 262 with a plurality of base members 264 and a retainer 266 with a plurality of retainer members 268 defined on the ends of base members 264. Each base member 264 includes a pivot point 270, and depending upon the width of the lip of the beverage container relative to the pivot points 270, each base member 264 will either rotate outwardly or inwardly. For wider beverage containers, e.g., mug 272, the lip is positioned radially outwardly from pivot points 270, causing outward rotation of each base member 264, with retainer members 268 positioned away from the beverage container. For narrower beverage containers, however, the lip may be positioned radially inwardly from pivot points 270, causing inward rotation of each base member 264, such that the weight of the beverage container urges the retainer members 268 against the sidewall of the beverage container.

Figure 14:
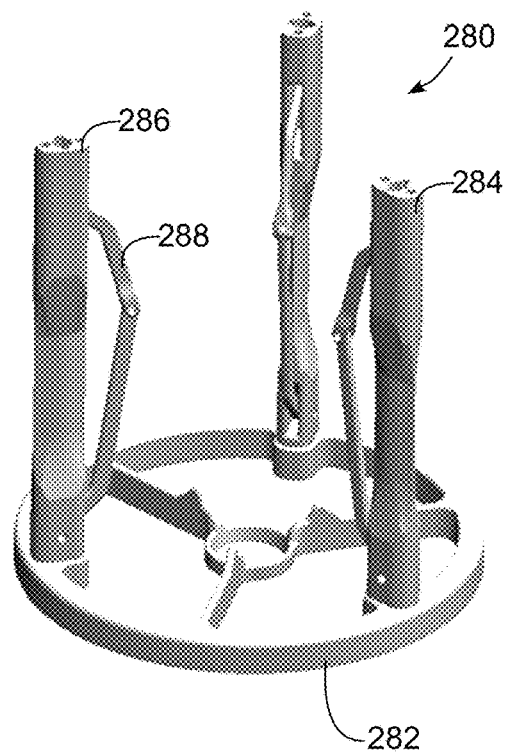

FIG. 14 illustrates a holder 280 including a base 282 similar to base 202 of holder 200 of FIG. 8, but with a retainer 284 formed by a set of vertical members 286 with spring-loaded supports 288 that are normally biased inwardly and configured to deflect radially outwardly when a beverage container is inserted downwardly into the holder.

Other holders may be used in other embodiments. Therefore, the invention is not limited to the particular holder designs illustrated herein.

Figure 15:
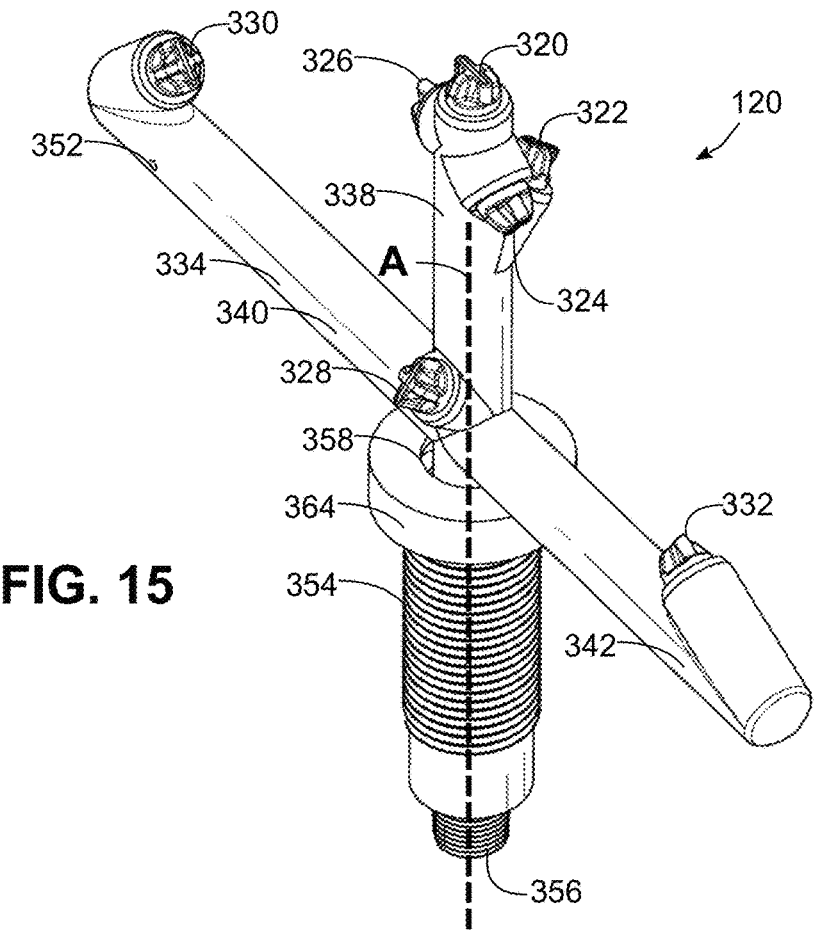
FIG. 15 is a perspective view of the sprayer of FIG. 4.

Now turning to FIG. 15, an example embodiment of sprayer 120 of washing station 110 (FIG. 4) is illustrated in greater detail. In the illustrated embodiment, sprayer 120 is a pop-up sprayer that is capable of rotating about an axis of rotation, which in the illustrated embodiment is coincident with axis of rotation A about which inner concentric housing member 62 rotates, as well as move between retracted and extended positions along the axis of rotation. Sprayer 120 includes a plurality of nozzles, e.g., seven nozzles 320, 322, 324, 326, 328, 330 and 332 in the illustrated embodiment, and as will become more apparent below, at least one of the nozzles (e.g., nozzle 320) is an interior nozzle oriented to spray wash fluid into an interior of a beverage container when the beverage container is held by the holder, and at least one of the nozzles (e.g., nozzle 330) is a lip nozzle oriented to spray wash fluid onto an outer lip of the beverage container when the beverage container is held by the holder.

Figure 16:
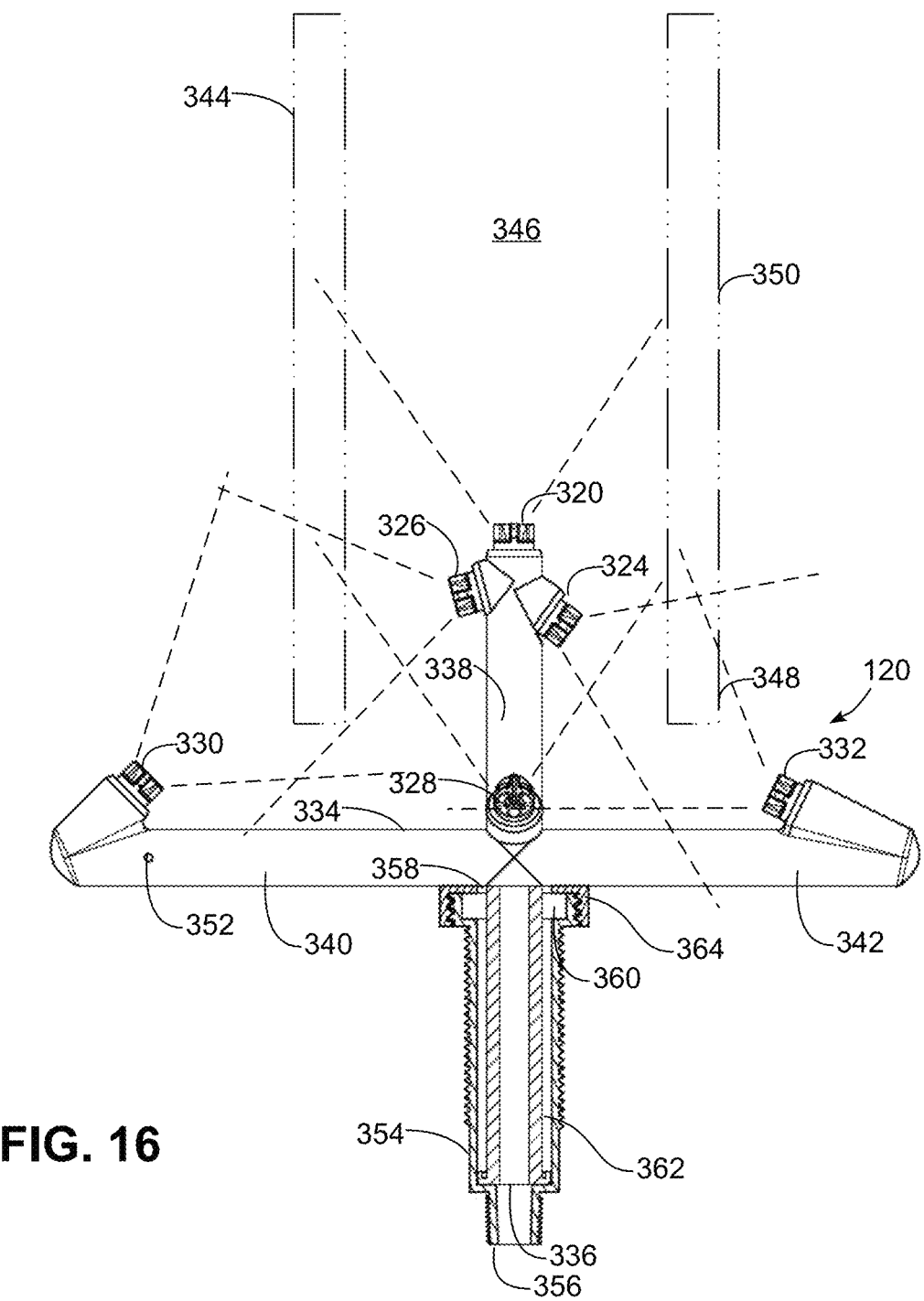
FIG. 16 is a side elevational view of the sprayer of FIG. 15, with a vertical cross section taken through the base thereof.

In the illustrated embodiment, and with additional reference to FIG. 16, nozzles 320-332 are supported by a manifold 334 including an inlet 336 configured to receive a pressurized wash fluid, an axial conduit 338 extending generally along the axis of rotation, and a pair of transverse conduits 340, 342 extending generally transverse to the axis of rotation, with each of conduits 338, 340, 342 in fluid communication with inlet 336.

Nozzles 320-328 are referred to herein as interior nozzles and are supported by, and in fluid communication with inlet 336 through, axial conduit 338, and at least a subset of these interior nozzles is axially offset from inlet 336 along the axis of rotation. While some of the wash fluid emitted by interior nozzles 320-328 may impact other regions of a beverage container (e.g., beverage container 344 of FIG. 16), interior nozzles 320-328 are primarily configured to spray wash fluid into the interior 346 of the beverage container, and as illustrated in FIG. 16, are generally arranged to provide overlapping spray patterns for different elevations within the interior of beverage container 344. The spray patterns may differ from one another along the axis of rotation, and the nozzles 320-328 may be axially and/or angularly offset from one another as shown in FIGS. 15 and 16.

In the illustrated embodiment, for example, interior nozzle 320 may be proximate a distal end of axial conduit 338 from inlet 336 and have a spray pattern with a center that is oriented along the axis of rotation. Interior nozzle 328 may be disposed proximate a junction between axial conduit 338 and transverse conduits 340, 342, and may have a spray pattern that is oriented to spray wash fluid onto the inner lip of the beverage container when the beverage container is held by the holder. Interior nozzles 322, 324 and 326 may also be positioned proximate the distal end of axial conduit 338, with interior nozzles 324 and 326 angularly offset from one another by about 180 degrees and having spray patterns oriented to spray wash fluid onto the inner lip of the beverage container when the beverage container is held by the holder, and interior nozzle 322 may have a spray pattern that is directed generally upwardly and overlaps the spray pattern of interior nozzle 320.

Nozzles 330, 332 are referred to herein as lip nozzles and are supported by, and in fluid communication with inlet 336 through, transverse conduits 340, 342, respectively. Each nozzle 330, 332 is radially offset from inlet 336 relative to the axis of rotation, and while some of the wash fluid emitted by lip nozzles 330, 332 may impact other regions of a beverage container, each lip nozzle 330, 332 is primarily configured to spray wash fluid at least partially onto an outer lip 348 of the beverage container 344, i.e., a portion of the beverage container lip or opening formed by an outer surface 350 of beverage container 344. As seen in FIG. 16, each lip nozzle 330, 332 may also focus spray onto other portions of the beverage container lip (e.g., an interior lip portion formed by an inner surface of the beverage container), and it will be appreciated that since it is generally the areas around the lip where a user's mouth may come into contact with the beverage container, lip nozzles 330, 332 in some embodiments may focus their efforts on spraying wash fluid at a sanitizing temperature to appropriately sanitize the areas of the beverage container that a user may likely come into contact with when drinking from the beverage container.

In the illustrated embodiment, transverse conduits 340, 342 are angularly offset from one another by about 180 degrees and both extend substantially normal to the axis of rotation. In other embodiments, different numbers of transverse conduits, e.g., as few as one or more than two, may be used, and the transverse conduits may extend at differing angles relative to the axis of rotation, so the invention is not limited to the particular configuration illustrated herein.

In addition, in the illustrated embodiment, sprayer 120 may additionally include one or more drive nozzles 352 that emit wash fluid in a tangential direction relative to the axis of rotation to drive rotation of sprayer 120 when spraying wash fluid. In other embodiments, the wash fluid sprayed by another nozzle 320-332 may impart sufficient torque to rotate the sprayer, and separate drive nozzles 352 may not be used. Further, in some embodiments an electric motor, pressurized air, or other electromechanical or mechanical drive system may be used to rotate the sprayer and/or move the sprayer between retracted and extended positions, whereby no separate drive nozzles 352 may be used.

Also in the illustrated embodiment, each nozzle 320-332 is a screw-in nozzle and is configured to threadably engage corresponding threaded apertures in manifold 334. As such, it may be desirable to form manifold 334 from a material capable of threadably engaging nozzles 320-332, e.g., metal. Each nozzle 320-332 also is configured with a fan spray pattern, e.g., with a spray width of about 15 to about 50 degrees in some embodiments. All nozzles 320-332 may be similarly configured in some embodiments, while in other embodiments, each nozzle 320-332 may include a different nozzle configuration tailored for its particular location and direction of spray. In the illustrated embodiment, the nozzles 320-332 are also clocked to a particular angle, e.g., such that the fan jets overlap and are all primarily oriented in the Y-plane. It will be appreciated that sprayer 120 may utilize different numbers, locations, types and configurations of nozzles in other embodiments, so the invention is not limited to the specific arrangement of nozzles illustrated herein. For example, in some embodiments, nozzles may be integrally molded into a manifold, and in some embodiments, different spray patterns, e.g., fluidic nozzles, jet nozzles, etc., may be used.

It will also be appreciated that, in the illustrated embodiment, sprayer 120 is predominantly limited to spraying wash fluid onto the interior of a beverage container as well as the inner and outer lip thereof (e.g., about 1 inch of the outer surface of the beverage container proximate the lip). While other regions of the outside of the beverage container may come into contact with wash fluid in some instances, the focus of sprayer 120 is on the areas of the beverage container that either come into contact with a beverage consumed by a user or come into contact with a user's mouth. Ultraviolet sanitizing assembly 32 instead focuses on the outer surface of a beverage container, including the outer lip; however, it is believed that limiting sprayer 120 to spraying the interior and outer lip of a beverage container with a wash fluid heated to a sanitizing temperature provides sufficient sanitization of a beverage container for many applications, and does so in a manner that reduces cycle time and water and energy consumption. In other embodiments, however, additional sprayers, e.g., located around the perimeter of the wash chamber, may be used to focus wash fluid onto the outside of a beverage container.

Manifold 334 is slidably received in a base 354. Base 354 includes an inlet 356 that receives pressurized wash fluid from pump 138, and an opening 358 that slidably and rotatably receives manifold 334. A seal 360 is disposed on base 354 to seal opening 358, while still allowing for slidable and rotary movement of manifold 334. A bias mechanism 362, e.g., a spring, is used to bias manifold 334, and thus sprayer 120, to a retracted position, e.g., as illustrated in FIGS. 15-16. However, manifold 334 is configured to overcome bias mechanism 362 and slide within base 354 to an extended position as a result of the pressure generated by wash fluid received through inlet 356 of base 354. Further details regarding sprayer 120 may be found in the aforementioned cross-referenced application.

It will be appreciated that, while certain features may be discussed herein in connection with certain embodiments and/or in connection with certain figures, unless expressly stated to the contrary, such features generally may be incorporated into any of the embodiments discussed and illustrated herein. Moreover, features that are disclosed as being combined in some embodiments may generally be implemented separately in other embodiments, and features that are disclosed as being implemented separately in some embodiments may be combined in other embodiments, so the fact that a particular feature is discussed in the context of one embodiment but not another should not be construed as an admission that those two embodiments are mutually exclusive of one another. Various additional modifications may be made to the illustrated embodiments consistent with the invention. Therefore, the invention lies in the claims hereinafter appended.

What is claimed is:

1. An apparatus for washing a beverage container, comprising:
   a housing;
   a holder disposed within the housing and configured to hold a beverage container during a wash cycle;
   a plurality of stations disposed within the housing, the plurality of stations including a first station for loading the beverage container into the holder and a second station configured to perform an operation on the beverage container during the wash cycle; and
   a holder transfer assembly supporting the holder and configured to transfer the holder between the plurality of stations, wherein the holder transfer assembly is further configured to spin the holder and thereby spin the beverage container during at least a portion of the transfer of the holder between the plurality of stations, wherein the holder transfer assembly includes:
   a holder support configured to rotatably support the holder;
   a holder support drive configured to move the holder support along a path extending between the plurality of stations;
   a pinion gear operably coupled to the holder to rotate with the holder; and
   a rack gear extending along at least a portion of the path extending between the plurality of stations and positioned to engage the pinion gear such that movement of the holder support along the path while the pinion gear engages the rack gear additionally rotates the holder.

2. The apparatus of claim 1, wherein the path and the rack gear are substantially linear and the holder support drive comprises a linear actuator.

3. The apparatus of claim 2, wherein the linear actuator comprises a screw drive.

4. The apparatus of claim 1, wherein the rack gear includes at least one toothless section such that no rotation of the holder occurs during movement of the holder support along the path proximate the toothless section of the rack gear.

5. The apparatus of claim 1, wherein the first station is a loading and unloading station.

6. The apparatus of claim 1, wherein the housing includes an entrance opening and an exit opening that is separate from the entrance opening, the entrance opening configured to receive a beverage container prior to the wash cycle and the exit opening configured to provide access to the beverage container after the wash cycle, wherein the first station is a loading station disposed proximate the entrance opening and the plurality of stations further comprises an unloading station disposed proximate the exit opening.

7. The apparatus of claim 1, wherein the second station comprises a washing station, an ultraviolet sanitizing station or a drying station.

8. The apparatus of claim 1, wherein the second station comprises a washing station and wherein the plurality of stations further comprises an ultraviolet sanitizing station or a drying station.

9. The apparatus of claim 1, wherein the second station comprises a washing station and wherein the plurality of stations further comprises an ultraviolet sanitizing and drying station.

10. The apparatus of claim 1, wherein the second station comprises an ultraviolet sanitizing station, and wherein the holder transfer assembly is configured to spin the holder and thereby spin the beverage container during at least a portion of the transfer of the holder through the ultraviolet sanitizing station.

11. The apparatus of claim 1, wherein the holder is configured to support the beverage container in an inverted orientation.

12. The apparatus of claim 1, wherein the holder is configured to receive the beverage container via manual insertion, and wherein the holder is configured to allow for manual removal of the beverage container.

13. The apparatus of claim 1, wherein the holder comprises:
   a base configured to support the beverage container when the beverage container is held by the holder in an inverted orientation; and
   a retainer configured to support a sidewall of the beverage container when the beverage container is held by the holder in the inverted orientation to restrict lateral movement of the beverage container during the washing cycle, the retainer including a lateral opening through which the beverage container may be passed during insertion into and/or removal from the holder.

14. The apparatus of claim 13, wherein the retainer includes a C-shaped retaining ring vertically separated from the base, and wherein the lateral opening is at least partially defined by an opening in the C-shaped retaining ring.

15. The apparatus of claim 14, wherein the retainer further includes first and second generally vertical supports supporting the C-shaped retaining ring and positioned on an opposite side of the base from the opening in the C-shaped retaining ring, and wherein the lateral opening is at least partially defined by the first and second generally vertical supports at an elevation below that of the C-shaped retaining ring such that a width of a first portion of the lateral opening below the C-shaped retaining ring is greater than a width of a second portion of the lateral opening defined by the opening in the C-shaped retaining ring.

16. The apparatus of claim 13, wherein the base includes an inclined portion defining a plurality of concentric annular supports, each of the plurality of concentric annular supports configured to center the beverage container in the holder when the beverage container is held by the bolder in the inverted orientation.

17. The apparatus of claim 13, wherein the base includes a plurality of steps defining a plurality of concentric annular supports, each of the plurality of concentric annular supports configured to center the beverage container in the holder when the beverage container is held by the holder in the inverted orientation.

18. An apparatus for washing a beverage container, comprising:
- a housing including an entrance opening and an exit opening that is separate from the entrance opening, the entrance opening configured to receive a beverage container prior to a wash cycle and the exit opening configured to provide access to the beverage container after the wash cycle;
- a holder disposed within the housing and configured to hold the beverage container during the wash cycle;
- a plurality of stations disposed within the housing, the plurality of stations including a loading station disposed proximate the entrance opening for loading the beverage container into the holder, an unloading station disposed proximate the exit opening for unloading the beverage container from the holder, at least one intermediate station between the loading and unloading stations and configured to perform an operation on the beverage container during the wash cycle; and
- a holder transfer assembly supporting the holder and configured to transfer the holder between the loading, at least one intermediate, and unloading stations, the holder transfer assembly further including:
  - a holder support configured to rotatably support the holder;
  - a holder support drive configured to move the holder support along a path extending between the plurality of stations;
  - a pinion gear operably coupled to the holder to rotate with the holder; and
  - a rack gear extending along at least a portion of the path extending between the plurality of stations and positioned to engage the pinion gear such that movement of the holder support along the path while the pinion gear engages the rack gear additionally rotates the holder.

* * * * *